US008389784B2

(12) United States Patent
Takai et al.

(10) Patent No.: US 8,389,784 B2
(45) Date of Patent: Mar. 5, 2013

(54) METHOD OF PRODUCING PROPYLENE CONTAINING BIOMASS-ORIGIN CARBON

(75) Inventors: Toshihiro Takai, Nishinomiya (JP); Daisuke Mochizuki, Mobara (JP); Michiaki Umeno, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 429 days.

(21) Appl. No.: 12/084,909

(22) PCT Filed: Nov. 13, 2006

(86) PCT No.: PCT/JP2006/322590
§ 371 (c)(1),
(2), (4) Date: May 13, 2008

(87) PCT Pub. No.: WO2007/055361
PCT Pub. Date: May 18, 2007

(65) Prior Publication Data
US 2008/0312485 A1 Dec. 18, 2008

(30) Foreign Application Priority Data

Nov. 14, 2005 (JP) .................... 2005-329023

(51) Int. Cl.
C07C 1/20 (2006.01)
C07C 6/04 (2006.01)
(52) U.S. Cl. ........ 585/315; 585/324; 585/640; 585/643; 585/644; 585/646; 585/820; 502/63
(58) Field of Classification Search .................. 585/315, 585/324, 640, 643, 644, 646, 820; 502/63
See application file for complete search history.

(56) References Cited

U.S. PATENT DOCUMENTS

| | | | |
|---|---|---|---|
| 4,451,566 A | 5/1984 | Spencer | |
| 4,575,575 A | 3/1986 | Drake et al. | |
| 4,684,760 A | 8/1987 | Drake | |
| 5,026,936 A * | 6/1991 | Leyshon et al. ............... | 585/315 |
| 5,120,894 A | 6/1992 | McCauley | |
| 6,358,482 B1 | 3/2002 | Chodorge et al. | |
| 2002/0147377 A1 | 10/2002 | Kanazirev | |
| 2003/0023125 A1 | 1/2003 | Euzen et al. | |
| 2003/0105376 A1* | 6/2003 | Foral et al. .................... | 585/804 |
| 2004/0254414 A1 | 12/2004 | Hildreth et al. | |
| 2005/0043574 A1 | 2/2005 | Powers et al. | |

FOREIGN PATENT DOCUMENTS

| | | |
|---|---|---|
| GB | 2 002 416 A | 2/1979 |
| JP | 48-16482 | 5/1973 |
| JP | 62-61639 | 3/1987 |
| JP | 62-197147 | 8/1987 |
| JP | 2002-253959 | 9/2002 |
| WO | WO-2005/063354 | 7/2005 |

OTHER PUBLICATIONS

"Kagaku Daijiten 1 Shukusatsuban Dai 32 Satsu", Kyoritsu Shuppan Co., Ltd., 1989 Nen, pp. 888, 889, 907, with translation.
"Kagaku Daijiten 7 Shukusatsuban Dai 32 Satsu", Kyoritsu Shuppan Co., Ltd., 1989 Nen, pp. 839, 840, 907, 908, with translation.
"Production of extra-fine polypropylene fibre, used in a battery separator, mask, various filters—from ethylene-propylene copolymer containing nucleating agent for forming beta crystal" Derwent, 1999, XP002310625.
"Propylene resin compsns, useful as adhesive for polyurethane foam,—comprises crysalline polypropylene, filler, elastomer, maleic anhydride-modified ethyleneU-propyleneU copolymer and hydroxyl gp(s)-terminated dieneU polymer", Derwent, 1996, XP002190491.
Communication (Supplementary European Search Report) in EP Appln No: 06 82 3364 dated Mar. 23, 2011.
Masubuchi, T. "Polyurethane elastomer compsoitions, used for e.g. car parts, comprises a polyurethane thermoplasti elastomer and a propylene mixture consisting of polypropylene and ethylene-propylene copolymer rubber", WPI/Thomson, Jul. 31, 2001, vol. 2001, No. 63, XP002526256.
Robert L. Banks et al., "New Developments and Concepts in Enhancing Activities of Heterogeneous Metathesis Catalysts", Journal of Molecular Catalysis, vol. 28, Nos. 1-3, Jan. 1985, pp. 117-131.
Schuchardt, et al. "A Indústria Petroquimica No Próximo Século: Como Substituir O Petróleo Como Matéria-primaΔ", QUIM. NOVA, 2001, vol. 24, No. 2, pp. 247-251.
Winter, et al. "Make ethylene from ethanol", Petrochemical Developments, Nov. 1976, pp. 125-133.
Wu, et al. "The Effect of Hydrogen on the Carbonaceous Layer Formed on Molybdenum Model Catalysts during High Temperature Propylene Metathesis", Journal of Catalysis, 1998, vol. 173, pp. 172-176.
Communication (Observation by Third Party) in EP Appln No. 06823364.2 dated Mar. 2, 2011.

* cited by examiner

Primary Examiner — Thuan D Dang
(74) Attorney, Agent, or Firm — Foley & Lardner LLP

(57) ABSTRACT

Ethanol obtained from ordinary biomass resources contains many impurities other than water and these impurities themselves or their decomposition products contaminate ethylene when the ethylene is produced by a dehydration reaction, whereby the activity of metathesis catalyst is adversely affected. A method for producing propylene of the present invention is characterized in that the ethanol obtained from biomass is converted to ethylene by a dehydration reaction, the ethylene is separated from the generated water, the separated ethylene is purified by adsorption in an adsorption tower filled with an adsorbent, and then a metathesis reaction is carried out along with a raw material containing n-butene. With the present invention, propylene having biomass-derived carbon and reduced-environmental burden can be efficiently produced without lowering the catalysis activity.

21 Claims, No Drawings

US 8,389,784 B2

METHOD OF PRODUCING PROPYLENE CONTAINING BIOMASS-ORIGIN CARBON

TECHNICAL FIELD

The present invention relates to a method for producing propylene containing carbon at least ⅓ of which is derived from biomass by a metathesis reaction of ethylene obtained from ethanol derived from biomass such as corn, sugarcane and the like with n-butene.

BACKGROUND ART

As a method for reducing carbon dioxide, one of the causes of global warming, the conversion from fossil resources to biomass resources is desired. Specifically, investigations have been carried out to use ethylene (1) obtained from methanol produced by a high-temperature gasification of biomass resources, or ethylene (2) obtained from ethanol produced by ferment of biomass resource by a dehydration reaction, as a substitute of ethylene produced by a naphtha cracker.

On the other hand, another important basic raw material for petrochemicals obtained from a naphtha cracker is propylene, and in order to produce propylene directly from methanol or ethanol, a conversion by a certain kind of chemical reaction is usually necessary. Here, a metathesis reaction, in which the same or different kinds of olefins are reacted to give an olefin having a different structure from those of the original ones, is generally very effective because ethylene is converted to propylene by reacting with 2-butene.

However, in general, a catalyst used in a metathesis reaction is extremely sensitive to water, an oxygen-containing compound and a nitrogen-containing compound, and thus deterioration of catalyst activity is developed immediately after a raw material containing these impurities is used. For example, a tungsten oxide catalyst which is a typical metathesis catalyst when used in a fixed bed reaction as disclosed in U.S. Pat. No. 4,575,575 (Patent Document 1) and in the Journal of Molecular Catalysis, Volume 28, page 117 (1985) (Non-Patent Document 1), is poisoned to a large extent by water present in raw materials. Therefore, it is considered necessary to purify butene of all the raw materials using an alumina as an adsorbent.

Ethylene, which is another raw material, is usually produced by a naphtha cracker. More specifically, nitrogen- and sulfur-containing impurities are removed from raw material naphtha and then the raw material is introduced into a naphtha cracker, and a high-temperature cracked gas obtained from the naphtha cracker is immediately cooled, alkali-washed, and purified by adsorption, and then separated into each component by respective distillation towers. Accordingly, the ethylene obtained from a naphtha cracker is not necessarily to be purified by adsorption when used in a metathesis reaction.

However, ethanol obtained from biomass resources, contains not only water but also a carbonyl compound that is an impurity from a fermentation process and a nitrogen-containing compound that is a decomposition product or a contaminant of an enzyme, and ethylene is contaminated by these compounds themselves or their decomposition products while obtaining the ethylene by a dehydration reaction, whereby the activity of a metathesis catalyst is adversely affected. Accordingly, development of a method for purifying the ethanol has been desired.

Patent Document 1: U.S. Pat. No. 4,575,575
Non-Patent Document 1: Journal of Molecular Catalysis, Volume 28, page 117 (1985)

DISCLOSURE OF THE INVENTION

Problems to be Solved by the Invention

An object of the present invention is to provide a method for producing propylene, in which a metathesis reaction is efficiently conducted by separating the ethylene obtained from biomass-derived ethanol from the generated water and then purifying by adsorption.

Means for Solving the Problems

The present inventors carried out extensive investigations to address the above-mentioned problems and found that propylene is efficiently obtained without inhibiting the activity of the metathesis reaction with n-butene by converting ethanol obtained from a biomass resource by a dehydration reaction to ethylene, and the ethylene is separated from the generated water and then purified by an adsorption tower packed with at least one kind of adsorbent selected from alumina, zeolite and MgO.

More specifically, the present inventors have found the effect of enhancement of the initial activity of the metathesis reaction with n-butene, namely an increase in propylene yield, and suppression of activity deterioration, namely elongation of the catalyst life, by purifying ethylene obtained from the ethanol obtained from a biomass resource by adsorption, and thus have completed the present invention having great industrial value.

That is, the present invention is as follows:

[1] A method for producing propylene containing biomass-derived carbon comprising converting ethanol obtained from biomass to ethylene by a dehydration reaction, separating the ethylene and a generated water and the like, and then purifying the separated ethylene by adsorption and performing a metathesis reaction with a raw material containing n-butene.

[2] The method for producing propylene according to the above [1], wherein the biomass-derived carbon accounts for ⅓ or more of a total carbon.

[3] The method for producing propylene according to the above [1], wherein an adsorbent containing at least one kind selected from alumina, magnesium oxide or a mixture thereof, and zeolite is used upon purifying the separated ethylene by adsorption.

[4] The method for producing propylene according to the above [3], wherein an adsorbent containing two or more kinds selected from alumina, magnesium oxide or a mixture thereof, and zeolite is used upon purifying the separated ethylene by adsorption.

[5] The method for producing propylene according to the above [1], wherein the metathesis reaction is carried out in the presence of a catalyst containing at least one kind of metal element selected from tungsten, molybdenum, rhenium, niobium, tantalum, vanadium, ruthenium, rhodium, iridium and osmium.

[6] The method for producing propylene according to the above [5], wherein a basic compound containing at least one kind of metal element of Group Ia (alkali metal), Group IIa (alkaline earth metal), Group IIb and Group IIIa is used as a promoter along with the catalyst used for the metathesis reaction.

[7] The method for producing propylene according to the above [6], wherein the promoter used for the metathesis reaction has a structure supporting the basic compound contain-

[8] The method for producing propylene according to the above [6], wherein at least one kind of metal element contained in the promoter used for the metathesis reaction is lithium, sodium, potassium, magnesium, calcium, yttrium or zinc.

[9] The method for producing propylene according to the above [8], wherein at least one kind of metal element contained in the promoter used for the metathesis reaction is lithium, sodium, or potassium.

[10] The method for producing propylene according the above [7], wherein the carrier that supports the promoter used for the metathesis reaction is alumina or zirconia.

[11] The method for producing propylene according to the above [5], wherein the catalyst used for the metathesis reaction has a structure supporting a compound containing at least one kind of metal element selected from tungsten, molybdenum, rhenium, niobium, tantalum, vanadium, ruthenium, rhodium, iridium and osmium on a carrier having a large surface area.

[12] The method for producing propylene according to the above [11], wherein the carrier supporting the catalyst used for the metathesis reaction is silica, alumina, or zirconia.

[13] The method for producing propylene according to the above [12], wherein at least one kind of metal element contained in the catalyst used for the metathesis reaction is tungsten.

[14] The method for producing propylene according to the above [1], wherein a hydrogen gas is co-present upon carrying out the metathesis reaction.

[15] The method for producing propylene according to the above [1], wherein one n-butene selected from the following (1) to (4) is used in the metathesis reaction:
(1) n-Butene containing no carbon derived from biomass resources obtained from a naphtha cracker and/or FCC;
(2) n-Butene obtained by dimerization of ethylene that is obtained from biomass-derived ethanol;
(3) n-Butene obtained by dehydration reaction of 1-butanol that is obtained by dehydration and dimerization of biomass-derived ethanol; and
(4) n-Butene obtained by dehydration reaction of a butanol mixture that is obtained from biomass resources.

[16] The method for producing propylene according to the above [15], wherein two or more kinds of n-butene selected from the above (1) to (3) are mixed and used in the metathesis reaction.

[17] The method for producing propylene according to the above [15], wherein n-butene according to the above (2) or (3) is further purified by adsorption and used in the metathesis reaction.

[18] The method for producing propylene according to the above [17], wherein an adsorbent containing at least one kind selected from alumina, magnesium oxide or a mixture thereof, and zeolite is used upon purifying the n-butene by adsorption.

[19] A high-purity propylene containing substantially no impurity due to ethanol obtained from biomass and containing biomass-derived carbon accounting for at least $1/3$.

[20] The high-purity propylene according to the above [19], wherein the high-purity propylene is used for a raw material of a polymer.

[21] A propylene polymer or a propylene copolymer containing one or more units of propylene having a biomass-derived carbon as a constitutional unit.

[22] An article comprising a resin composition containing the polymer or the copolymer according to the above [21].

[23] A method for continuously producing propylene containing a biomass-derived carbon, comprising the steps of:
(1) dehydrating ethanol obtained from biomass by a dehydration reactor;
(2) separating and removing water, unreacted ethanol and a by-product in ethylene obtained by the dehydration reactor;
(3) removing by adsorption an impurity in an obtained crude ethylene by passing the obtained crude ethylene through an adsorption tower; and
(4) introducing purified ethylene and n-butene into a metathesis reactor; (with the proviso that the order is (1) to (4)),
in the method for producing propylene according to the above [1].

[24] The method for continuously producing propylene according to the above [23], further comprising the steps of:
(5) introducing the propylene obtained from the metathesis reactor into an ethylene stripping tower to remove materials having a low boiling point containing ethylene as a main component; and
(6) introducing propylene free from materials having a low boiling point into a propylene stripping tower to remove materials having a high boiling point; (with the proviso that the order is (5) to (6)).

[25] The method for continuously producing propylene according to the above [24], further comprising the steps of:
(7) recycling the off-gas having a low boiling point from the ethylene stripping tower to the metathesis reactor; and
(8) recycling the n-butene component in an off-gas having a high boiling point from the propylene stripping tower to the metathesis reactor; (with the proviso that the order is (7) to (8)).

[26] The method for continuously producing propylene according to the above [23], wherein n-butene used for the metathesis reaction is produced by:
(a) dehydrating butanol by a dehydration reactor;
(b) separating and removing water, unreacted butanol and a by-product in n-butene obtained by the dehydration reactor; and
(c) purifying the n-butene by adsorption in an adsorption tower;
(with the proviso that the order is (a) to (c)).

[27] The method for continuously producing propylene according to the above [26], wherein butanol is derived from biomass, and n-butene after the purification by adsorption is introduced into the stage after the metathesis reaction and before the purification of a low-boiling point component.

Effects of the Invention

According to the present invention, even when biomass-derived ethanol is used as a raw material, deterioration of the catalyst activity of the metathesis reaction is suppressed. Therefore, the switch-over frequency of reactors is reduced and high-quality propylene is produced in high yield in a remarkably advantageous way from the viewpoint of processing and economy. The propylene is extremely useful in view of the balance of carbon dioxide in the environment, and thus remarkably contributes to the global environment even when used as derivatives or polymers.

BEST MODE FOR CARRYING OUT THE INVENTION

In the following, the present invention will be explained in detail.

In the present invention, ethanol obtained from a biomass resource refers to the ethanol produced by bringing a culture solution containing carbon sources that is convertible to ethanol and obtained from a plant into contact with an ethanol-producing microorganism or a crushed product therefrom, and then purified.

As for a carbon source, there is no particular restriction as far as the carbon source is obtained from a plant and is convertible to ethanol by microbial metabolism, and there may be mentioned, as a typical example, starch, glucose, fructose, sucrose, xylose, arabinose, or degradation products of plants, hydrolysis products of cellulose or juice of sugarcanes, beet and the like containing large amounts of the above components.

To the culture solution, phosphoric acid, inorganic salts such as an ammonium salt and the like for a nitrogen source, corn steep liquor, peptone, natural nitrogen sources such as yeast extract and the like, a vitamin, and others, if necessary may be added.

Furthermore, as a microorganism producing ethanol, there is no specific restriction as far as it produces ethanol, and as a typical example, *Saccharomyces cerevisiae*, *Zymomonas mobilis* and the like may be mentioned, and in addition, it is further preferred that one or more properties selected from the heat resistance, the acid resistance, the salt resistance, the agglutinability, and the alcohol resistance are imparted by utilizing such technologies as mutation, genetic recombination and the like.

In order to obtain ethanol from the culture solution containing ethanol obtained as above, conventionally known purification technologies such as distillation, membrane separation, extraction and the like can be used, and also there may be mentioned a method of removing water using an azeotropic distillation involving addition of benzene, cyclohexane and the like, a membrane separation and others. Such ethanol may be purchased as fermented ethanol 99%, first grade from Nippon Alcohol Hanbai Co., Ltd., and as fermented ethanol from Petrobras S. A.

It is not necessarily effective from the industrial viewpoint to further perform advanced purification of ethanol at this stage (for example, total content of impurities in ethanol is 1 ppm or less) in order to obtain propylene of the present invention, but this advanced purification is not excluded altogether.

Next, to obtain ethylene by the dehydration reaction of ethanol obtained by a fermentation method, a catalyst is usually used, and as for the catalyst, there is no particular restriction and any publicly known catalyst may be used. As an advantageous processing, a fixed bed flow reaction is preferred in view of easy separation of catalyst and a product. For example, γ-alumina and the like are preferable, but other publicly known catalysts may also be used. This reaction is a dehydration reaction, and is usually carried out with heating. Although there is no specific restriction with regard to the reaction temperature as far as the reaction progresses at a commercially practical rate, the temperature at 100° C. or higher is preferable. There is no specific restriction with regard to the reaction pressure, either, but in order to facilitate the subsequent gas-liquid separation, the pressure at normal pressure or higher is preferable. From the industrial viewpoint, a fixed bed flow reaction is preferable because of easy separation of the catalyst, but a liquid phase suspension bed, a fluidized bed and the like may also be used. Particularly the dehydration reaction using a solid catalyst is industrially advantageous, because water contained in ethanol, if any, does not cause a significant problem. An acceptable range of water content is 50 wt % or less, and preferably 30 wt % or less.

By performing the dehydration reaction of ethanol as above, a mixture of ethylene, water, and a small amount of unreacted ethanol is obtained, and ethylene is obtained by removing water and ethanol from the mixture by a gas-liquid separation, because ethylene is in a gaseous state under about 5 MPa or less at room temperature. This procedure may be carried out using a publicly known method.

Ethylene obtained by the gas-liquid separation may be further distilled, and there is no particular restriction with regard to the distillation method, the operation temperature, the residence time and the like except that the operational pressure is normal pressure or higher.

The obtained ethylene contains as impurities a very minute amount of carbonyl compounds such as a ketone, an aldehyde, an ester and the like which have mixed in during the ethanol fermentation process, carbon dioxide which is a decomposition product of the carbonyl compounds, a nitrogen-containing compound such as an amine, an amino acid and the like which is a decomposition product or a contaminant of an enzyme, and ammonia which is a decomposition of the nitrogen-containing compound, and others. The metathesis reaction is very sensitive to these impurities, resulting in decrease of the catalyst activity, and thus it is required that a very minute amount of these impurities is removed completely, preferably to a level of 10 ppm or less as total amount of impurities containing oxygen, nitrogen and sulfur, and more preferably 1 ppm or less. It should be noted that a conventional analytical instrument often fails to detect impurities at the above-mentioned level. In such a case, there is no choice but to judge the presence or absence of the impurities by the duration of the catalyst activity.

A purification method by adsorption may be mentioned as used for the most suitable purification operation. The adsorbent to be used is preferably made of a material having a large surface area of 10 m$^2$/g or more, and preferably 50 m$^2$/g or more.

The most suitable adsorbent to be used is γ-alumina, which is particularly suitable for the removal of neutral polar substances such as water and alcohol. Also, magnesium oxide or a mixture thereof with another adsorbent, or an adsorbent having magnesium oxide supported on a carrier having a large surface area such as γ-alumina is suitable for removal of not only neutral polar substances such as water and the like but also acidic substances such as carbon dioxide, an organic acid and the like. Also, zeolite compounds, for example, Molecular Sieve 4A, 5A and the like are not only excellent in adsorption of neutral polar substances such as water and the like but also very effective in adsorbing basic compounds because acidic property is exerted by changing a changeable metal of zeolite to a proton or a divalent metal such as Ca and the like. Suitable examples of zeolite skeletons used in such a way include an A type, an X type, a Y type, a USY type, a ZSM-5 type and the like, but are not restricted to these.

Because these adsorbents are used in any methods of a fixed bed, a suspension bed, and a moving bed, their forms may be selected appropriately from particles of several centimeters to fine powders of a micron order.

As mentioned above, the kind of an adsorbent is selected in accordance with the kind and amount of impurities in ethylene obtained by the dehydration reaction of biomass-derived ethanol, and there is a case where preferably two or more kinds of adsorbents are used in combination. Also, an adsorbent other than the above (for example, deoxygenating agents such as copper oxide/aluminum oxide and the like, and others), may be used in a mixture or singly in a connected way.

A fixed bed is convenient for the design of an adsorption tower because an amount of an adsorbent is chosen in accordance with the amount of an acidic substance such as carbon dioxide, a neutral substance such as water, and a basic substance such as ammonia. Particularly, when two or more kinds of adsorbents are packed in a fixed bed, they may be packed in a mixture. However, by packing adsorbents in layers and monitoring the inner temperature, the state of adsorption of each poisoning substance to the adsorbents may be estimated.

In addition, there is no particular restriction with regard to the operational temperature of adsorption, but is preferably 100° C. or lower in general because a low temperature is preferable in adsorption-desorption equilibrium. Also, there is no particular restriction with regard to the pressure at the time of adsorption as far as the pressure is normal pressure or higher. For regeneration of the adsorption tower used for absorption treatment of ethylene, there may be mentioned a method in which adsorbed substances are desorbed by introducing an inert gas heated to a high temperature of 200° C. or higher, a method in which an air heated to a high temperature of 300° C. or higher is introduced for burning and calcinations, then the air is replaced with an inert gas, and the like. These methods may be selected in accordance with accumulated amounts of adsorbed substances in the adsorption tower.

Particularly installation of plural adsorption towers in parallel is highly advantageous industrially, because continuous adsorption is performed by an adsorption treatment in one tower while conducting a regeneration operation in another tower, and by switching the operation to the completely-regenerated adsorption tower immediately after the performance of the adsorption tower in use is decreased. Installation of three or more adsorption towers further contributes to a stable operation because it is also possible to replace an adsorbent whose prescribed adsorption capacity is lost after a long-term operation.

From the industrial viewpoint, purification of ethylene by adsorption at this stage is far more efficient than carrying out the advanced purification at the stage of ethanol in order to obtain ethylene having about the same degree of purity. Also, regardless of whether or not the advanced purification has been done at the stage of ethanol, impurities adversely affecting the metathesis reaction can be satisfactorily removed by performing the purification at this stage.

In addition, a caustic water treatment may also be used in combination as a method for purifying impurities in ethylene. When performing the caustic water treatment, it is preferable to perform the caustic water treatment before the purification by adsorption. In such a case, it is necessary to perform a water-removal treatment after the caustic water treatment and before the purification by adsorption.

On the other hand, butenes used as a raw material together with ethylene may be a single kind of each n-butene, namely, 1-butene, trans-2-butene and cis-2-butene, or a mixture thereof, and are used as raw materials for the metathesis reaction even when linear olefins such as 1-pentene, 2-pentene, 1-hexene, 2-hexene, 3-hexene and the like are contained. Furthermore, although not converting to propylene by the metathesis reaction, even when branched olefins such as isobutene, isopentene and the like are contained, the metathesis reaction is not disturbed. Furthermore, saturated hydrocarbons such as n-butane, iso-butane, pentane and the like, and inert gases such as nitrogen and the like may be mixed in.

Any of the following methods may be applied to obtain n-butene to be used for the metathesis reaction. The most convenient is the C4 fraction that is obtained from: what is called a naphtha cracker, in which naphtha is thermally cracked to produce ethylene and propylene; what is called a FCC, in which heavy oil is thermally decomposed by catalysts such as zeolite and the like; and others. This C4 fraction usually contains iso-butene, n-butane, iso-butane and the like other than 1-butene and 2-butene, but there is no particular problem. Also, even when 1-pentene, 2-pentene and the like are contained, there is no harm since they are used as the raw material for the metathesis reaction. However, conjugated dienes such as butadiene, cyclopentadiene and the like significantly impair the metathesis catalyst activity, thus it is necessary to remove them by publicly known methods such as adsorption, distillation, extraction and the like, or to convert them to monoolefins by selective hydrogenation in advance.

Next mentioned is the method for making n-butene by the dimerization of ethylene that is obtained from biomass-derived ethanol, and any publicly known methods can be used for it. There may be mentioned a catalyst having $NiSO_4$ supported on silica gel in the case of a fixed bed catalyst, a combination catalyst of $NiCl_2(PPh_3)_2$ and $Et_3Al$, in the case of homogeneous catalyst, and others.

Also, n-butene obtained by dehydration reaction of a mixture of 1-butanol and 1,3-butadiene that are obtained by bringing biomass-derived ethanol into contact with a transition metal-containing hydroxyapatite catalyst or by a selective hydrogenation reaction of a diene to a monoene may be used, as disclosed in Japanese Patent Laid-Open Publication No. H11-217343 and Japanese Patent Laid-Open Publication No. 1999-038822.

Furthermore, it is also possible to use n-butene obtained by dehydration of 1-butanol obtained by fermentation of biomass resources. Here, 1-butanol obtained by fermentation of biomass resources means the one which is obtained by bringing a culture solution containing carbon sources derived from a biomass which is capable of converting to butanol into contact with microorganisms that produce butanol. Generally, acetone and ethanol are co-produced. As carbon sources, there is no particular restriction as far as they are derived from a biomass and are capable of converting to butanol by microbial metabolism, but typical examples include starch, glucose, fructose, sucrose, xylose, arabinose, or degradation products of plants, hydrolysis products of cellulose or juice of sugarcanes, beet and the like containing a large amount of these components.

To the culture solution, phosphoric acid, inorganic salts such as an ammonium salt and the like for a nitrogen source, corn steep liquor, peptone, natural nitrogen sources such as yeast extract and the like, a vitamin, and others, may be added if necessary.

As a microorganism that produces butanol, there is no specific restriction as far as it produces butanol, and typical examples include *Enterobacter aerogenes, Clostridium butylicum, Clostridium beijerinckii, Clostridium saccharoper-butylacetonicum* and the like and it is further preferable that they should be imparted one or more properties selected from the heat resistance, the acid resistance, the salt resistance, the agglutinability, and the alcohol/acetone resistance by using such technologies as mutation, genetic recombination and the like. In order to purify the butanol from the culture solution containing butanol obtained as above, conventionally known technologies such as distillation, membrane separation, extraction and the like may be used.

Prior to using in the metathesis reaction, it is necessary to remove water and polar substances from n-butene, which is conducted by publicly known methods such as distillation, adsorption, extraction, washing and the like. Particularly, n-butene containing carbon sources derived from a plant, as well as ethylene obtained from biomass-derived ethanol, contains a very minute amount of impurities that adversely affect the metathesis reaction. Therefore, it is preferable to employ correspondingly a purification method used for ethanol.

When carrying out the metathesis reaction by using ethylene and n-butene, the molar ratio in a reactor may be arbitrary, but it is usually preferable to use an excessive amount of ethylene, and the amount ratio of ethylene to n-butene is preferably 0.1 to 50 and more preferably about 0.5 to 5. When the amount ratio of ethylene is low, an undesirable reaction between butene molecules themselves also occurs simultaneously, and when the amount ratio is too high, energy for the recovery of unreacted ethylene is increased and a reactor itself grows in size. Ethylene and n-butene may be charged in all together with an olefin having high amount ratio, or charged fractionally through feeding inlets provided at a middle stage and the like of the reactor in addition to the entrance of the reactor.

A metathesis catalyst used in the present invention contains at least one kind of publicly known metal element selected from tungsten, molybdenum, rhenium, niobium, tantalum, vanadium, ruthenium, rhodium, iridium, osmium, nickel and the like, and tungsten, molybdenum and rhenium have a high catalyst activity, among them tungsten is particularly preferable.

Its structure may be a simple substance in a solid state in the composition composed of oxide, sulfide, hydroxide and the like of each metal, and may be a structure supporting these metal oxides, sulfides, hydroxides and the like on an inorganic compound having a large surface area, what is called a carrier. When used in a fixed bed flow reaction, those in the form of oxide are preferable because they are regenerated by calcinations with an air after deterioration.

Furthermore, acidic nature of the carrier causes unwanted side reactions such as oligomerization of olefins and the like, thus any material may be used as far as it has no acidic nature. More specifically, a carrier having a surface area of $10\,m^2/g$ or more is preferable, and silica, γ-alumina, titania and the like may be mentioned as preferable examples. Among them silica is selected as a suitable carrier because silica has a particularly large surface area. In such a case, the supported amount of metal relative to the carrier is preferably in the range of 0.01% to 50% and far preferably in the range of 0.1% to 20% in terms of oxide equivalent.

Among the above-mentioned metal compounds, as to the method for supporting an oxide onto a carrier, any publicly known methods may be used, and a metal nitrate or hydroxide, and in the case of tungsten, molybdenum, and rhenium, their polyacids and isopolyacids, an ammonium salt of the polyacids, and an ammonium salt of isopolyacids are used as starting materials, and in the aqueous solutions, carrier is immersed, or evaporated to dryness, and then the resultant is calcinated at 300° C. or higher under an air atmosphere to obtain.

A commercially available carrier may be used as it is, but a carrier may be obtained as an oxide by calcinating a hydroxide that is obtained by making a corresponding metal salt basic in accordance with a publicly known method. A co-deposition method may be employed, in which synthesis of a carrier and metal supporting are performed simultaneously in the co-presence of a metal salt for the catalyst at the time of producing a carrier from the corresponding metal salt.

A shape of a carrier is not particularly restricted, any of sphere, column, extruded, and crushed shapes may be used. The particle size may be selected in the range of 0.01 mm to 100 mm depending on the size of a reactor.

Furthermore, in order to make metal element compounds such as tungsten, molybdenum, rhenium, niobium, tantalum, vanadium, ruthenium, rhodium, iridium, osmium, nickel and the like soluble in an organic solvent, a complex catalyst bonding to an organic molecule called a ligand may be used. Also, the ones that are supported onto a carrier for easy recovery may be used.

In particular, it is preferable to use a promoter in this metathesis reaction because the activity increases. Specific examples of such promoters include those containing at least one metal element in Group Ia (alkali metals), Group IIa (alkaline earth metals), Group IIb and Group IIIa, and specific examples of such metal elements include lithium, sodium, potassium, cesium, magnesium, calcium, strontium, barium, zinc, yttrium and the like.

In any of U.S. Pat. Nos. 4,575,575, 4,754,098, and 4,88, 760 by Phillips Petroleum Company, a promoter containing magnesium oxide is mentioned as an essential component, but in the present invention magnesium oxide is not necessarily essential. Lithium, sodium and potassium may be mentioned as far preferable examples from the viewpoint of catalyst activity.

These compounds may be a simple substance in the solid state having a composition of an oxide, a hydroxide, a nitrate salt, an acetate salt and the like, or may be a compound in which these metal compounds further contain other metal compounds, that is, a hydrotalcite in which aluminum and magnesium form a layered compound as oxides of each metals and a composite oxide such as solid solution of aluminum oxide and magnesium oxide. Furthermore, the ones supporting an oxide, a composite oxide, a hydroxide, a nitrate salt, an acetic salt and the like of these metals onto an inorganic compound having a large surface area called a carrier may also be used.

Taking into account that an acidic nature of a carrier causes unwanted side-reactions such as olefin oligomerization and the like, any one may be used as far as the carrier does not exhibit acidic nature after a metal element in Group Ia (alkali metals), Group IIa (alkaline earth metals), Group IIb and Group IIIa is supported. More specifically, a carrier having a surface area of $10\,m^2/g$ or larger is preferable, and γ-alumina, zirconia, titania and the like are mentioned as a preferable example. Furthermore, magnesium oxide itself may be used as a carrier because of having a large surface area. Particularly, from the viewpoint of chemical stability, γ-alumina is a preferable carrier. In this case, the supported amount of metal relative to the carrier is in the range of 0.01% to 50% and preferably in the range of 0.1% to 20% in terms of oxide.

A commercially available carrier may be used as it is, but a carrier may be obtained as an oxide by calcinating a hydroxide that is obtained by making a corresponding metal salt basic in accordance with a publicly known method.

Any publicly known method may be used for supporting an oxide of the above-mentioned metal compound onto a carrier, in which a carrier is immersed in an aqueous solution of a metal nitrate salt or a metal hydroxide, or an aqueous suspension of an oxide, or evaporated to dryness, and then the resultant is calcinated at 300° C. or higher under an air atmosphere.

Furthermore, a co-deposition method may be employed, in which synthesis of a carrier and metal supporting are performed simultaneously in the co-presence of a metal salt for the catalyst at the time of producing a carrier from the corresponding metal salt.

A shape of a carrier is not particularly restricted, any of sphere, column, extruded, and crushed shapes may be used. The particle size may be selected in the range of 0.01 mm to 100 mm depending on the size of a reactor.

Furthermore, when a catalyst in which a metal element such as tungsten and the like is supported onto a carrier and a catalyst in which a metal element such as sodium, magnesium and the like is supported onto a carrier are used in combination, a metal element such as tungsten and the like and a meal element such as sodium, magnesium and the like may be supported simultaneously onto one kind of carrier.

An amount of a promoter relative to a catalyst may be chosen arbitrarily in the range of 0.1 to 20. However, when the amount is extremely small, the effect of hydrogenation is not obtained, and when the amount is extremely large, the catalyst ratio is lowered and the activity relative to the total amount of the catalyst and the promoter decreases, and thus it is not preferred. Furthermore, when packing a catalyst into a fixed bed flow reactor, a physically blended mixture of a catalyst and a promoter may be packed, as described in the Journal of Molecular Catalysis, Volume 28, page 117 (1985), or a promoter and a catalyst may be packed in this order from the side near the raw material feeding inlet. In addition, a combination of these methods and the like may be mentioned.

Furthermore, the activity is further increased by carrying out the metathesis reaction in the presence of hydrogen gas. Usually, hydrogen is continuously charged in the gaseous state, but charging is not limited to this method. Hydrogen may be charged intermittently, in which charging of hydrogen gas is done at the initiation of the reaction and stopped during the reaction, and then restarted after a certain interval, and in the case of a reaction in a liquid phase, hydrogen gas may be dissolved in a solvent and then charged. Furthermore, in a recycle process, the hydrogen gas recovered from a top of a tower together with a fraction of low boiling point may be charged. Although there will be an effect of hydrogen addition at the very beginning by charging into a reactor a hydrogen gas remaining after the replacement of hydrogen gas used for a reduction treatment of catalyst with nitrogen gas, the activity gradually decreases because no new hydrogen is charged, thereby ultimately leading to the same performance as the reaction without charging hydrogen gas, and thus durable effects are not obtained as in the present invention.

The hydrogen pressure to be added is generally the same as that in a reactor, but it may be changed depending on a method for charging hydrogen.

The amount of the hydrogen to be added relative to the total gases is in the range of 0.1 to 80% by volume and preferably 0.2 to 50% by volume, when the raw materials charged into a reactor are counted as gases. When the amount is smaller than the range, the effect by the addition is not achieved, and when the amount is larger, partial pressures of olefin raw materials are reduced and hydrogenation reaction of olefins takes place simultaneously, thus it is not preferred.

The temperature of the metathesis reaction is not particularly restricted in the present invention, but preferably in the range of 100 to 500° C. and more preferably 130 to 350° C. When the reaction temperature is extremely low, the reaction rate is lowered, and thus the productivity of the reaction product is reduced. On the other hand, when the reaction temperature is extremely high, unwanted side reactions and the like progress, in which by-products are increased and catalyst deterioration is accelerated, and thus are not economical.

The metathesis reaction may be carried out under any of reduced, elevated, and normal pressures. In view of reaction efficiency (reaction efficiency per unit volume), it is not preferred to carry out the reaction under extremely low pressure. Usually practical pressure is preferably in the range of 0.1 to 200 atm and more preferably 0.5 to 100 atm. It should be noted that the present invention is not limited to these pressure ranges.

The amount of a catalyst to be used for carrying out the metathesis reaction is not particularly restricted, but when the reaction is carried out by using a fixed bed flow reactor, the value of the weight of the charging amount (by mass) of raw materials per unit time over the weight of catalyst alone containing tungsten and the like and not containing a promoter, namely WHSV, is preferably in the range of 1 to 2000/h and more preferably 2 to 1000/h. When WHSV is excessively low, the target olefin product thus obtained causes sequential metathesis reactions and the unwanted by-products are produced, and when WHSV is excessively high, sufficient conversion rate may not be obtained.

The present invention may also be performed in a diluted state by adding into a reaction system a solvent or a gas inert to the catalyst and reaction agents. Specifically, alkanes such as methane, ethane, propane, butane and the like mentioned above, and inert gases such as nitrogen, helium and the like may also be used as a diluent.

When carrying out the metathesis reaction, any of a batch system, a semi-batch system, or a continuous flow system may be used. The metathesis reaction can also be carried out in any of a liquid phase, a gas phase, and a mixed gas-liquid phase. Preferably, in view of the reaction efficiency, a method for performing in a gas phase reaction is recommended. As a method for packing the catalyst, various methods such as a fixed bed, a fluidized bed, a suspension bed, a shelf-type fixed bed and the like may be employed and any of them may be used.

After the metathesis reaction, the target propylene is separated and recovered by a publicly known separation method from the above-mentioned catalyst and the like. Furthermore, a reaction mixture containing the produced propylene may be separated by publicly known methods such as distillation, extraction, adsorption and the like, and unreacted ethylene and n-butene may be recovered and recycled again to be used as raw materials in the reaction system.

When performing the metathesis reaction, it is preferable to dehydrate a catalyst and a promoter by a publicly known method. In the case of a fixed bed reaction method, the reaction is satisfactorily performed by keeping a reactor packed with a catalyst and a promoter at 300° C. or higher for 10 minutes or longer while flowing inert gases such as nitrogen, helium and the like through the reactor. Particularly, in the case where the metal element contained in a catalyst is tungsten or molybdenum, a reduction treatment may be performed after the above operation by flowing reducing gases such as carbon monoxide and hydrogen through the reactor at 300° C. or higher for 10 minutes or longer, again flowing an inert gas through the reactor at 300° C. or higher for 10 minutes or longer, and then the temperature is set at a predetermined reaction temperature. Because the present reaction is characterized by the co-existence of hydrogen, when hydrogen is used in the reduction treatment, the hydrogen may remain. When the catalyst activity decreases after a certain period of time, the catalyst activity may be recovered by regeneration. In general, after adsorbed olefins are purged with nitrogen gas, the catalyst is oxidized by air or nitrogen-diluted air at 300° C. or higher, further subjected to the reduction treatment by reducing gases such as hydrogen, carbon monoxide and the like in the case where the metal is tungsten or molybdenum, and then the catalyst is used again.

In order to maintain production quantity of olefin by metathesis reaction, a merry-go-round system may be used, in which two or three reactors are installed in parallel and while regenerating one reactor, the metathesis reaction is carried out in the other one or two reactors. Furthermore, when there are three reactors, a method in which the other two reactors are connected in series to reduce fluctuation of production quantity may be employed. Furthermore, when performing a fluidized bed flow reaction method or a moving bed reaction method, a certain level of catalyst activity is maintained by withdrawing part or all of the catalyst from a reactor continuously or intermittently and replenishing the corresponding quantity. Similarly, when a suspension bed reaction method is performed in batch or continuous reaction, the catalyst is separated and recovered in a similar manner, and may be used after being regenerated if necessary.

Furthermore, biomass-derived butanol contains acetone and ethanol as major impurities. These impurities are converted to propylene and ethylene respectively after a dehydration reaction and purification by adsorption. Because these olefins are raw materials and products of the metathesis reaction, the off-gas after the dehydration/purification may be charged in the stage after the metathesis reaction and before the purification of a mixture of raw materials and propylene.

In the case of a continuous production of propylene including a recycle system, it is preferable to install a storage tank at each stage before recycling because the adjustment of raw material composition is necessary.

Propylene obtained in accordance with the present invention, having an extremely small amount of biomass-derived impurities, can also be used as a polymer raw material that requires high purity in the same way as with propylene derived from an oil resource.

A polymer and a copolymer composed of propylene obtained in accordance with the present invention are a polymer containing carbons derived from plant. Although the environmental burden in material recycling is extremely low as compared with a polymer composed of propylene derived from naphtha, they have physical properties equivalent to those of conventional polymers derived from naphtha and are very useful. As a polymer or a copolymer of propylene, a homopolypropylene, a random polypropylene, an isotactic polypropylene, a syndiotactic polypropylene, a propylene-α-olefin copolymer, a propylene-based elastomer, a propylene-based rubber and the like are exemplified. These may be further modified.

Further, although a polyol and a polyurethane whose starting raw material is propylene oxide produced from propylene obtained in accordance with the present invention also have extremely low environmental burden in material recycling, they have physical properties equivalent to those of polymers composed of raw materials derived from naphtha and are very useful.

These polymers and copolymers composed of propylene, and polyurethanes and polyols may be used singly or as a mixture with other thermoplastic polymers such as a polyolefin, a polystyrene, a polyester, a polyamide, a polyurethane, a polyacrylic acid copolymer and the like. Particularly, their co-use with a polymer or copolymer composed of ethylene produced from biomass-derived alcohol is very useful from the viewpoint of environmental burden. Furthermore, to the above-mentioned polymer and copolymer may be added publicly known conventional additives, for example, a plasticizer, a ultraviolet absorber, an antistatic agent, an anti-oxidant, a lubricant, a stabilizer, inorganic fillers and the like.

A composition containing a polymer or copolymer composed of propylene obtained in accordance with the present invention is processed into various articles, for instance, those obtained by an injection molding, an extrusion molding, a blow molding, a press molding and the like similar to a composition containing a polymer or copolymer composed of conventional propylene derived from naphtha, and physical properties of the articles are equivalent to those of conventional ones. Furthermore, these articles may be recycled similarly to conventional ones.

The fact that propylene obtained by the method of the present invention or a polymer such as polypropylene and the like produced by using propylene as a raw material utilizes a biomass raw material is judged by measuring contents of carbons having mass number 14 and contents of carbons having mass number 12 or mass number 13.

Specifically, the judgment can be made by burning a sample to obtain $CO_2$ in accordance with ASTM (American Society for Testing and Materials) D6866 04 (Standard Test Methods for Determining the Biobased Content of Natural Range Materials Using Radiocarbon and Isotope Ratio Mass Spectrometry Analysis), introducing the $CO_2$ gas accurately and quantitatively analyzed into an AMS (Accelerated Mass Spectrometry) instrument to measure quantities of carbons having mass number 14, and mass number 12 or mass number 13, and then comparing with the existence ratio of the carbon having mass number 14 present in air or in a petrochemical product.

Furthermore, the judgment can be made by burning a sample to obtain $CO_2$, and absorbing the obtained $CO_2$ by a $CO_2$ absorbent or converting to benzene, measuring the quantity of carbon having mass number 14 with a liquid scintillation counter, and comparing with those derived from petroleum.

In the following, Examples of the present invention are described, but the present invention is not restricted by these Examples.

EXAMPLE 1

Synthesis of Biomass-Derived Ethylene

Into the center of a SUS-made reactor of a pressurized flow instrument having the outer diameter of 20 mm and the length of 80 cm was charged 100 ml of activated alumina (NKHD 24, manufactured by Sumitomo Chemical Co., Ltd.) and then nitrogen gas under normal pressure at the rate of 200 mL/min at 500° C. for 2 hours from the top of the reactor, and then the temperature was lowered to 350° C. Biomass-derived ethanol (ethanol content of 92%, manufactured by Petrobras S. A.) was charged at the rate of 20 g/h from the top of the reactor. The exit line at the bottom of the reactor is connected to a back-pressure regulating valve adjusted at 0.5 MPa through a SUS-made trap (volume of 500 mL), and the water produced by the reaction and unreacted ethanol are collected by ice-cooling the outside of the SUS-made trap during the reaction, while produced ethylene goes through the back-pressure regulating valve in gas state to a compressor, where the ethylene is compressed to 5 MPa and collected as a liquefied ethylene into a liquefied gas vessel. The weight of ethylene collected in the liquefied gas vessel after 10 hours was 119 g with the conversion rate of 99% or more and the yield of 99%.

Synthesis of Biomass-Derived Propylene

A SUS-made reactor having the outer diameter of 12 mm and the length of 40 cm were packed in order starting from the bottom to the top with 5 g of hydrotalcite (Kyowardo 500, 500μ, manufactured by Kyowa Chemical Industry Co., Ltd.), 5 g of γ-alumina (activated alumina, manufactured by Sumitomo Chemical Co., Ltd.), and 5 g of HZSM-5 Zeolite (manufactured by Sud-Chemie AG), and both the upper and lower ends were packed with α-alumina balls to make an ethylene purification column. 0.83 g of ammonium metatungstate (manufactured by Aldrich Inc.) was dissolved in 100 mL of distilled water, and 5 g of Silica Gel Q-10 (surface area of 300 m$^2$/g, pore volume of 1 mL/g, 150 to 500 p, manufactured by Fuji Silysia Chemical Ltd.) was suspended. The mixture was stirred at room temperature for 30 minutes, and then water was removed by an evaporator. The obtained white solid was calcinated in air atmosphere at 550° C. for 6 hours. The catalyst thus obtained is named WQ-10.5 g of WQ-10 and 10 g of hydrotalcite (Kyowardo 500, 500 p, manufactured by Kyowa Chemical Industry Co., Ltd.) are physically mixed, and the mixture was packed into a SUS-made reactor having the outer diameter of 18 mm and the length of 400 mm. Both the upper and lower ends were packed with α-alumina balls to make a butene purification column. Then, 0.5 g of WQ-10 and 2.4 g of hydrotalcite were physically mixed and the mixture was packed into the center of the SUS-made reactor having the outer diameter of 18 mm and the length of 400 mm. Both the upper and lower ends were packed with α-alumina balls to make a reactor.

Nitrogen gas under normal pressure was charged in the reactor from the top at 100 mL/min, and the gas discharged from the bottom was charged through the butene purification column from the bottom to the top, and then further was charged through the ethylene purification column from the bottom to the top, and the reactor, the butene purification column, and the ethylene purification column were all heated to 500° C. and the temperature was kept for one hour. Then, hydrogen gas under normal pressure was flowed at 100 mL/min at the same temperature for 120 minutes. While flowing nitrogen gas and hydrogen gas under the normal pressure at 50 mL/min, the reactor was cooled to 200° C. and the butene and the ethylene purification columns to 50° C.

Prior to use, distilled liquefied trans-2-butene (99% purity, manufactured by Takachiho Chemical Industrial Co., Ltd.) was flowed onto γ-alumina (NKHD-32, manufactured by Sumitomo Chemical Co., Ltd.) at the rate of 0.10 g/min by using a plunger pump through the butene purification column from the bottom to obtain liquefied pure trans-2-butene from the top. The liquefied pure trans-2-butene was combined with the purified ethylene obtained in gas state from the top of the ethylene purification column, into which the liquefied ethylene had been charged from the bottom at the rate of 64.5 mL/min after the pressure was adjusted to 3.5 MPa at the exit of the liquefied gas vessel and the hydrogen which was pressurized to 3.5 MPa and charged at the rate of 7.0 mL/min, and the combined mixture was charged from the top of the reactor in gas state after passing through a preheated layer heated to 200° C. When the gas mixture obtained from the bottom of the reactor returned to the state of the normal pressure through the back-pressure regulating valve, the on-line analysis by a gas chromatography was performed. From the composition 10 hours after the initiation of the reaction, the butene conversion rate obtained by subtracting the total amount of tras-2-butene, cis-2-butene and 1-butene contained in the outlet gas from the charged trans-2-butene was 71%. The propylene selectivity based on butene at this time was 90% and small amounts of pentene and hexene were produced in addition. At this time, propane was produced simultaneously along with propylene and the ratio of propane to propylene was 0.01. Furthermore, the reaction continued for another 12 hours, but the decrease in the butene conversion rate was not observed.

REFERENCE EXAMPLE 1

Quantitative Analyses of N Component and S Component
(Analysis Method of an Ethanol Sample)
Quantitative analysis of N component: The total N components contained in a sample were quantitatively analyzed by using a total nitrogen analyzer.
[Instrument] Total Nitrogen Analyzer; TN-10, manufactured by Mitsubishi Chemical Corp.
Quantitative analysis of S component: A sample was decomposed at 900° C. under the Ar/O$_2$ atmosphere, and the generated gas was absorbed in an absorbing liquid to obtain a sample solution. The SO$_4$ ion component in the sample solution was quantitatively analyzed by an ion chromatography, and then converted to the S component.
[Instrument] Ion chromatograph: DX-500 manufactured by Dionex Corp.
(Analysis Results)
Biomass-derived ethanol manufactured by Petrobras S.A, 92% purity:
N component 1.5 ppm, S component 4 ppm
Biomass-derived ethanol manufactured by Petrobras S.A, 99% purity: N component 2.3 ppm, S component 4 ppm
Reagent grade ethanol: N component <1 ppm, S component <2 ppm
Biomass-derived ethanol (manufactured by Petrobras S.A, 92% purity) and biomass-derived ethanol (manufactured by Petrobras S.A, 99% purity) were respectively subjected to the dehydration reaction and purification by adsorption in a similar manner to that of Example 1. Analyses after each process showed that the N component and the S component in ethylene gas after the purification by adsorption were below the detection limit for each component.

REFERENCE EXAMPLE 2

Final Off-Gas Composition of Example 1
The off-gas composition after the metathesis reaction in Example 1 was as follows.

| | |
|---|---|
| Propylene: | 51.2% by volume |
| Ethylene: | 36.1% by volume |
| Butene: | 11.6% by volume |
| Others: | 12.7% by volume |

EXAMPLE 2

The dehydration reaction, the purification of ethylene by adsorption and the metathesis reaction were performed in a similar manner as in Example 1 except that biomass-derived ethanol purchased from Nippon Alcohol Hanbai Co., Ltd. (99%, first grade) was used instead of the biomass-derived ethanol in Example 1. After 10 hours, quantity of ethylene collected in the liquefied gas vessel was 109 g with the ethylene conversion rate of 95% and the ethylene yield of 90%. The butene conversion rate obtained in the metathesis reaction by analyzing the gas at the exit one hour after the initiation of the reaction was 71%. The durability of the catalyst activity was equivalent to that in Example 1.

EXAMPLE 3

After the reactor, the butene purification column and the ethylene purification column were subjected to the pretreatment and the reduction treatment in a similar manner as those of Example 2, by flowing nitrogen at 100 mL/min, the reactor was cooled to 250° C., and both the butene and ethylene purification columns to 50° C., and ethylene and trans-2-butene at the same ratio as in Example 1 were charged through the reactor without flowing hydrogen. The butene conversion rate obtained by analyzing the gas at the exit one hour after the initiation of the reaction was 71%. The durability of the catalyst activity was equivalent to that of Example 1.

EXAMPLE 4

The metathesis reaction was carried out in a similar manner to that of Example 2 except that 25 g of γ-alumina was used instead of the adsorbent for the ethylene purification column in the article of Synthesis of Biomass-derived Propylene. The butene conversion rate obtained by analyzing the gas at the exit one hour after the initiation of the reaction was 71%. The durability of the catalyst activity was equivalent to that of in Example 1.

EXAMPLE 5

The metathesis reaction was carried out in a similar manner to that of Example 2 except that 25 g of hydrotalcite was used instead of the adsorbent for the ethylene purification column in the article of Synthesis of Biomass-derived Propylene. The butene conversion rate obtained by analyzing the gas at the exit one hour after the initiation of the reaction was 70%. The durability of the catalyst activity was equivalent to that of Example 1.

EXAMPLE 6

The metathesis reaction was carried out in a similar manner to that of Example 2 except that 12 g of H-ZSM-5 Zeolite and 12 g of MS4 Å molecular sieve were used instead of the adsorbent for the ethylene purification column in the article of Synthesis of Biomass-derived Propylene. The butene conversion rate obtained by analyzing the gas at the exit one hour after the initiation of the reaction was 70%. The durability of the catalyst activity was equivalent to that of Example 1.

EXAMPLE 7

15 g of γ-alumina (NKHD-32, surface area of 250 m$^2$/g, manufactured by Sumitomo Chemical Co., Ltd.) was suspended into a solution containing 0.08 g of sodium hydroxide (manufactured by Wako Pure Chemical Industries, Ltd.) dissolved in 500 mL of distilled water. The mixture was stirred at room temperature for 30 minutes and then water was distilled out with an evaporator. The obtained white solid was calcinated in air atmosphere at 550° C. for 6 hours. The reaction was carried out in a similar manner to that of Example 1 except that 2.4 g of thus obtained solid was used instead of hydrotalcite and that the reaction temperature was 175° C. The butene conversion rate obtained by analyzing the gas at the exit 10 hours after the initiation of the reaction was 69%. Furthermore, the propylene selectivity was 94%. Small amounts of pentene and hexane were also generated. In addition, propane was generated concurrently with propylene and the ratio of propane/propylene was 0.0066. The reaction was continued for another 12 hours but no decrease in the butene conversion rate was observed.

EXAMPLE 8

Production of Acetone-Butanol-Ethanol by *Clostridium Beijerinckii*

10 mL of a sterilized preculture solution (1% tripton (manufactured by Difco Corp.), 0.5% yeast extract (manufactured by Difco Corp.), 0.5% glucose) was charged into a sterilized test tube, and one platinum loop of *Clostridium beijerinckii* (ATCC10132) was inoculated, then the tube was stood still at 37° C. for 2 days and precultured. The obtained preculture solution was transferred to a BMS-10 type stainless steel culture vessel (manufactured by Biott Corp.) containing 7 L of the sterilized culture solution as shown in Table 1. Then, inside of the culture vessel was purged with sterilized nitrogen, the inner pressure was adjusted to a state of more than 0.005 MPa by using a pressure control valve with sterilized nitrogen, then the cultivation was performed at a stirring rate of 150 rpm at 35° C. for 3 days.

After the cultivation was finished, microbial bodies were removed by centrifugation to obtain 6.5 L of supernatant. The obtained supernatant was fractionally distilled by distillation equipment to the fractions of acetone, ethanol, water, and butanol, and each fraction was distilled respectively to obtain 63 g of crude butanol, 31 g of crude acetone, and 6 g of crude ethanol.

It should be noted that *Clostridium beijerinckii* (ATCC10132) is obtained from American Type Culture Collection as ATCC10132.

TABLE 1

| Medium Component | |
|---|---|
| Glucose | 60 g/L |
| Ammonium acetate | 2 g/L |
| KCl | 0.5 g/L |
| KH$_2$PO$_4$ | 0.5 g/L |
| K$_2$HPO$_4$.3H$_2$O | 0.38 g/L |
| MgSO$_4$.7H$_2$O | 0.2 g/L |
| MnSO$_4$.H$_2$O | 10 mg/L |
| Fe$_2$SO$_4$.7H$_2$O | 10 mg/L |
| p-Aminobenzoic acid | 1 mg/L |
| Biotin | 0.01 mg/L |
| (Rest of the medium:water) | pH 6.8 |

Synthesis of Biomass-Derived n-Butene 100 mL of activated alumina (NKHD 24, manufactured by Sumitomo Chemical Co., Ltd.) was packed into the center of a pressurized SUS-made flow reactor having the outer diameter of 20 mm and the length of 80 cm and nitrogen gas under normal pressure was flowed through from the top of the reactor at 200 mL/min at 500° C. for 2 hours, and then the temperature was cooled to 350° C. The obtained crude butanol mentioned above was charged in from the top of the reactor at the rate of 10 g/h. The exit line at the bottom of the reactor was connected to a back-pressure valve set at 0.15 MPa via a SUS-made trap (volume of 500 mL), water generated from the reaction and unreacted butanol were collected by ice-cooling the SUS-made trap from outside during the reaction. The generated n-butene was collected in a liquefied gas vessel cooled at the dry ice temperature after passing through the back-pressure regulating valve in gas state. After 20 hours, the weight of n-butene collected in the liquefied gas vessel was 42 g and the yield was 88%.

Synthesis of Biomass-Derived Propylene

The metathesis reaction was carried out in a similar manner to that of Example 2 except that the obtained biomass-derived n-butene as described above was purified by using one additional adsorption column which was the same as the one used for purification of biomass-derived ethylene in Example 1. The butene conversion rate obtained by analyzing the gas at the exit one hour after the initiation of the reaction was 71%. The durability of the catalyst activity was equivalent to that in Example 1.

EXAMPLE 9

Synthesis of n-Butene from Biomass-Derived Ethanol

Biomass-derived ethanol used in Example 1 was subjected to the dimerization reaction under the conditions described in J. Mol. Catal., 251 (2003), 337 to obtain biomass-derived n-butanol. The conversion rate was 48% and the yield was 19%. The dehydration reaction was carried out in a similar manner to that of Example 8 except that the obtained biomass-derived n-butanol was used. The weight of n-butene collected in the liquefied gas vessel was 40 g and the yield was 84%.

Synthesis of Biomass-Derived Propylene

The metathesis reaction was carried out in a similar manner to that of Example 2 except that the obtained biomass-derived n-butene as described above was purified by using one additional adsorption column which was the same as the one used for purification of biomass-derived ethylene in Example 1. The butene conversion rate obtained by analyzing the gas at the exit one hour after the initiation of the reaction was 71%. The durability of the catalyst activity was the same as in Example 1.

COMPARATIVE EXAMPLE 1

The metathesis reaction was carried out in a similar manner to that of Example 1 except that ethylene obtained from a commercially available high-purity liquefied ethylene cylinder was introduced directly into the reactor without passing through the ethylene purification column instead of the ethylene obtained from biomass-derived ethanol in Example 1. The butene conversion rate calculated from the composition at the exit after 10 hours from the initiation of the reaction was 71%. The propylene selectivity based on butene at this time was 90% and small amounts of pentene and hexene were generated in addition. Furthermore, propane was generated concurrently with propylene and the ratio of propane/propylene was 0.01. After this, the reaction was continued for another 12 hours but no decrease in the butene conversion rate was observed.

COMPARATIVE EXAMPLE 2

In preparation of biomass-derived propylene described in Example 2, the reaction was carried out by introducing biomass-derived ethylene directly into the metathesis reactor without any purification by adsorption. The butene conversion rate obtained by analyzing the gas at the exit one hour after the initiation of the reaction was only 8%.

COMPARATIVE EXAMPLE 3

A similar operation to that of Comparative Example 2 was performed except for using purified ethanol which was obtained by refluxing biomass-derived ethanol (99%, first grade, purchased from Nippon Alcohol Hanbai Co., Ltd.) in reflux equipment packed with molecular sieves for 1 hour, cooling to the room temperature and then performing filtration through silica gels and activated carbons. The butene conversion rate obtained by analyzing the gas at the exit one hour after the initiation of the reaction was only 10%.

EXAMPLE 10

Products obtained according to Examples 1 to 9 are all collected by a dry ice-cooled trap after flowing out from the back-pressure regulating valve to obtain propylenes, butenes as liquefied gases. 420 g of accumulated liquefied gas collected was distilled under pressurized condition to obtain 200 g of biomass-derived propylene gas. The propylene purification column that was prepared by packing 20 g of γ-alumina into a SUS-made reactor (12 mm×400 mm) was calcinated at 550° C. for 5 hours under nitrogen stream, and then after cooling to the room temperature, biomass-derived propylene was flowed for the use in the following polymerization operation.

Preparation of Solid-State Titanium Catalyst Component (A)

A mixture of 95.2 g of anhydrous magnesium chloride, 442 mL of decane, and 390.6 g of 2-ethylhexylalcohol was heated at 130° C. for 2 hours to obtain a homogeneous solution. In this solution, 21.3 g of phthalic anhydride was added and the resulting mixture was stirred and mixed at 130° C. for another one hour for dissolution.

After the homogeneous solution thus obtained was cooled to the room temperature, 30 mL of this homogeneous solution was added dropwise into 80 mL of titanium tetrachloride ($TiCl_4$) kept at −20° C. over one hour. The obtained mixture solution was heated up to 110° C. over four hours, and 2.1 g of diisobutyl phthalate (DIBP) was added when the temperature reached 110° C., and at this temperature the solution was kept for two hours under stirring. After the reaction was finished, the solid component was collected by hot-filtration, re-suspended in 110 mL of $TiCl_4$, and then the obtained suspension was heated again at 110° C. for two hours. After the reaction, the solid component was collected again by hot-filtration and then thoroughly washed with decane and hexane heated at 110° C. until no free titanium compounds were detected in the washing solution. The solid-state titanium catalyst component obtained as above was kept as hexane slurry. Part of the hexane slurry of the solid-state titanium catalyst component was collected and dried, and then a composition of the catalyst component was analyzed. The solid-state titanium catalyst component (A) contained 2.2 wt % of titanium, 19.0 wt % of magnesium, 59.0 wt % of chlorine, and 19.8 wt % of DIBP.

Preparation of Preliminary Polymerization Catalyst Component (1)

In a four-neck glass reactor of 200 mL volume equipped with a stirrer, under nitrogen atmosphere, 100 mL of purified hexane, 3 mmol of triethylaluminum, and 1.0 mmol, based on titanium atom, of the solid state titanium catalyst component (A) obtained above were added, and then propylene was fed at the rate of 3.2 Nl/h at 20° C. for one hour.

When the propylene charge was finished, a gas inside the reactor was replaced by nitrogen, and then the supernatant solution was removed and the purified hexane was added for washing. These operations were performed twice, and thus obtained preliminary polymerization catalyst component (1) was re-suspended in purified hexane and the whole quantity of liquid was transferred into a catalyst vessel.

Polymerization

In a nitrogen-replaced autoclave of 1 L volume, 400 mL of purified heptane was charged, and then at 60° C. under propylene atmosphere, 0.4 mmol of triethylaluminum (TEA), 0.4 mmol of dicyclopentyl dimethoxy silane (DCPMS), and 0.008 mmol, based on titanium atom, of the preliminary polymerization catalyst (1) obtained above were charged.

After 100 mL of hydrogen was introduced, the temperature was heated to 70° C., and kept at this temperature for one hour to polymerize propylene. During the polymerization, the pressure was kept at 5 kg/cm² G. After the polymerization, slurry containing solid product was filtrated to separate white powders from a liquid phase, and then the white powders were dried for 10 hours under reduced pressure to obtain 112 g of polypropylene containing a biomass resource by ⅓.

INDUSTRIAL APPLICABILITY

Propylene containing biomass-derived carbons by ⅓ or more is produced by the method of the present invention industrially. The propylene is very useful in view of carbon dioxide balance in the environment, and greatly contributes to the global environment also as the derivative or polymer.

The invention claimed is:

1. A method for producing propylene containing biomass-derived carbon comprising:
    converting ethanol obtained from biomass to ethylene by a dehydration reaction;
    separating the ethylene, generated water, unreacted ethanol and a by-product;
    purifying the separated ethylene by adsorption, in which an adsorbent containing a deoxygenating agent comprising copper oxide and aluminum oxide
    is used to obtain an ethylene containing a ketone, an aldehyde and an ester which have been mixed in during the ethanol fermentation process, carbon dioxide which is a decomposition product thereof, an amine and an amino acid which is decomposition product or a contaminant of an enzyme, and ammonia which is a decomposition thereof in an amount of 10 ppm or less as total amount; and then
    performing a metathesis reaction with a raw material containing n-butene.

2. The method for producing propylene according to claim 1, wherein the biomass-derived carbon accounts for ⅓ or more of a total carbon.

3. The method for producing propylene according to claim 1, wherein the metathesis reaction is carried out in the presence of a catalyst containing at least one kind of metal element selected from tungsten, molybdenum, rhenium, niobium, tantalum, vanadium, ruthenium, rhodium, iridium and osmium.

4. The method for producing propylene according to claim 3, wherein a basic compound containing at least one kind of metal element of Group Ia (alkali metal), Group IIa (alkaline earth metal), Group IIb and Group IIIa is used as a promoter along with the catalyst used for the metathesis reaction.

5. The method for producing propylene according to claim 4, wherein the promoter used for the metathesis reaction has a structure supporting the basic compound containing one metal element of Group Ia (alkali metal), Group IIa (alkaline earth metal), Group IIb and Group IIa on a carrier having a large surface area.

6. The method for producing propylene according to claim 4, wherein at least one kind of metal element contained in the promoter used for the metathesis reaction is lithium, sodium, potassium, magnesium, calcium, yttrium or zinc.

7. The method for producing propylene according to claim 6, wherein at least one kind of metal element contained in the promoter used for the metathesis reaction is lithium, sodium, or potassium.

8. The method for producing propylene according claim 5, wherein the carrier that supports the promoter used for the metathesis reaction is alumina or zirconia.

9. The method for producing propylene according to claim 3, wherein the catalyst used for the metathesis reaction has a structure supporting a compound containing at least one kind of metal element selected from tungsten, molybdenum, rhenium, niobium, tantalum, vanadium, ruthenium, rhodium, iridium and osmium on a carrier having a large surface area.

10. The method for producing propylene according to claim 9, wherein the carrier supporting the catalyst used for the metathesis reaction is silica, alumina, or zirconia.

11. The method for producing propylene according to claim 10, wherein at least one kind of metal element contained in the catalyst used for the metathesis reaction is tungsten.

12. The method for producing propylene according to claim 1, wherein a hydrogen gas is co-present upon carrying out the metathesis reaction.

13. The method for producing propylene according to claim 1, wherein one n-butene selected from the following (1) to (4) is used in the metathesis reaction:
    (1) n-Butene containing no carbon derived from biomass resources obtained from a naphtha cracker and/or FCC;
    (2) n-Butene obtained by dimerization of ethylene that is obtained from biomass-derived ethanol;
    (3) n-Butene obtained by dehydration reaction of I-butanol that is obtained by dehydration and dimerization of biomass-derived ethanol; and
    (4) n-Butene obtained by dehydration reaction of a butanol mixture that is obtained from biomass resources.

14. The method for producing propylene according to claim 13, wherein two or more kinds of n-butene selected from the above (1) to (3) are mixed and used in the metathesis reaction.

15. The method for producing propylene according to claim 13, wherein n-butene according to the above (2) or (3) is further purified by adsorption and used in the metathesis reaction.

16. The method for producing propylene according to claim 15, wherein an adsorbent containing at least one kind selected from alumina, magnesium oxide or a mixture thereof, and zeolite is used upon purifying the n-butene by adsorption.

17. A method for continuously producing propylene containing a biomass-derived carbon, comprising the steps of:
    (1) dehydrating ethanol obtained from biomass by a dehydration reactor;
    (2) separating and removing water, unreacted ethanol and a by-product in ethylene obtained by the dehydration reactor;
    (3) removing by adsorption an impurity in an obtained crude ethylene by passing the obtained crude ethylene through an adsorption tower; and
    (4) introducing purified ethylene and n-butene into a metathesis reactor; (with the proviso that the order is (1) to (4), in the method for producing propylene according to claim 1.

18. The method for continuously producing propylene according to claim 17, further comprising the steps of:
    (5) introducing the propylene obtained from the metathesis reactor into an ethylene stripping tower to remove materials having a low boiling point containing ethylene as a main component; and (6) introducing propylene free from materials having a low boiling point into a propylene stripping tower to remove materials having a high boiling point; (with the proviso that the order is (5) to (6)).

19. The method for continuously producing propylene according to claim 18, further comprising the steps of:
(7) recycling the off-gas having a low boiling point from the ethylene stripping tower to the metathesis reactor; and
(8) recycling the n-butene component in an off-gas having a high boiling point from the propylene stripping tower to the metathesis reactor; (with the proviso that the order is (7) to (8)).

20. The method for continuously producing propylene according to claim 17, wherein n-butene used for the metathesis reaction is produced by:

(a) dehydrating butanol by a dehydration reactor;
(b) separating and removing water, unreacted butanol and a by-product in n-butene obtained by the dehydration reactor; and
(c) purifying the n-butene by adsorption in an adsorption tower; (with the proviso that the order is (a) to (c)).

21. The method for continuously producing propylene according to claim 20, wherein butanol is derived from biomass, and n-butene after the purification by adsorption is introduced into the stage after the metathesis reaction and before the purification of a low-boiling point component.

* * * * *

UNITED STATES PATENT AND TRADEMARK OFFICE
CERTIFICATE OF CORRECTION

| | |
|---|---|
| PATENT NO. | : 8,389,784 B2 |
| APPLICATION NO. | : 12/084909 |
| DATED | : March 5, 2013 |
| INVENTOR(S) | : Takai et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 536 days.

Signed and Sealed this
Thirtieth Day of December, 2014

Michelle K. Lee
*Deputy Director of the United States Patent and Trademark Office*